Aug. 31, 1965 E. S. BOERNER Plant Pat. 2,549
ROSE PLANT
Filed April 29, 1964
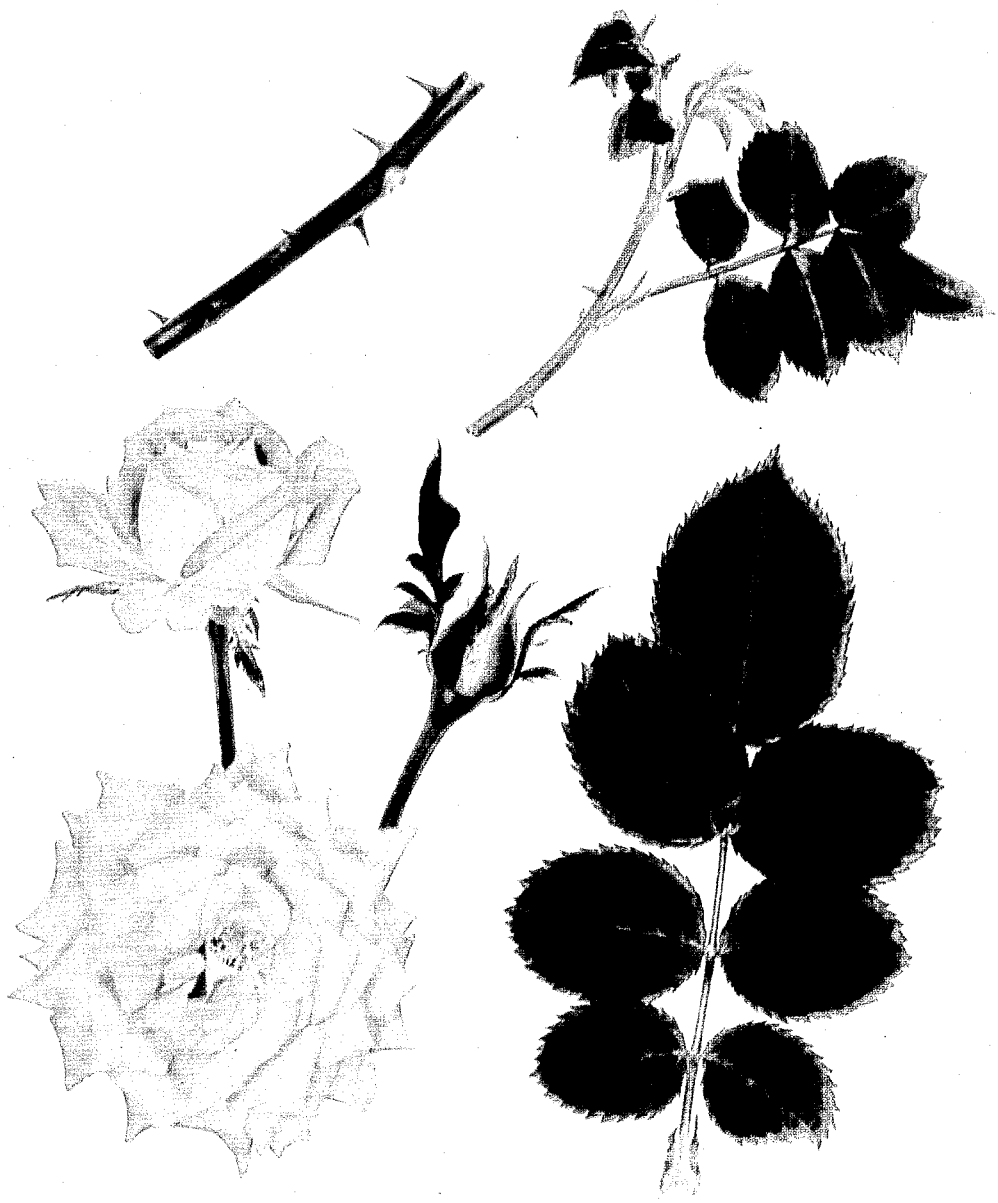
Inventor
E. S. Boerner
By: Robb & Robb
Attorneys.

United States Patent Office

Plant Pat. 2,549
Patented Aug. 31, 1965

2,549
ROSE PLANT

Eugene S. Boerner, Newark, N.Y., assignor to Jackson & Perkins Company, Newark, N.Y., a corporation of New York Filed Apr. 29, 1964, Ser. No. 363,689
1 Claim. (Cl. Plt.—22)

The present invention relates to a new and distinct variety of rose plant of the floribunda class, which was originated by me as a selfed seedling resulting from a cross of the floribunda variety known as "Jingles" (Plant Patent No. 1,570) with itself.

The primary objective of this breeding was to produce a new rose variety generally corresponding to the variety "Jingles," but which bears flowers of different color. This objective was fully achieved, along with other desirable improvements, as evidenced by the following unique combination of characteristics which are outstanding in the new variety and which distinguish it from its parents, as well as from all other varieties of which I am aware:

(1) Prolific production of cut flowers;

(2) An attractive and distinctive general color tonality of the flowers, with the inside of the flower petals being Rose Red and the reverse side being Marguerite Yellow, faintly overcast with La France Pink; and (3) Long-lasting flower qualities.

Asexual reproduction of my new variety by budding, as preformed at Newark, New York, and also at Pleasanton, California, shows that the aforementioned characteristics and distinctions come true to form and are established and transmitted through suceeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Jingles."
*Pollen parent.*—"Jingles."
Classification:
*Botanic.*—Floribunda.
*Commercial.*—Floribunda.

*Flower*

(Observations made from specimens grown in greenhouse at Newark, New York, during the early morning around the first part of the month of July.)

Blooming habit: Recurrent—continuous.
Bud:
*Size.*—Medium.
*Form.*—Ovoid; is not affected by wet or hot weather.
*Color.*—When sepals first divide—Spinel Red, Plate 26. When petals begin to unfurl—Spinel Pink, Plate 26, with lower half of petal overcast with Pinard-Yellow, Plate 4. When half-brown: inside of petals—Rose Red, Plate 12, with lower half of petal lightly overcast with Pale Greenish Yellow, Plate 5; reverse of petals—Shrimp Pink, Plate 1, faintly overcast with Eosine Pink, Plate 1, and the lower half of the petal being overcast with Picric Yellow, Plate 4.
*Sepals.*—Branched; "hood" above bud; curl back when petals begin to unfurl. Color: inside—Pale Turtle Green, Plate 32; outside—Deep Dull Yellow-Green (1), Plate 32, overcast with Victoria Lake, Plate 1.
*Calyx.*—Color—Deep Dull Yellow-Green (1), Plate 32. Shape — funnel. Size — small. Aspect — smooth. Odor when rubbed—none.
*Peduncle.*—Length — medium. Aspect — prickly. Color—Cress Green, Plate 31. Strength—erect; slender.
*Opening.*—Opens up well; is not affected by adverse weather conditions.

Bloom:
*Size.—Medium.* Average size when fully expanded—3 inches.
*Borne.*—Both singly and several together; prolific production of cut flowers.
*Stems.*—Medium length; strong.
*Form (when first open).*—Cupped. Permanence—flattens.
*Petalage.*—Double (full but open center). Number of petals under normal conditions—40.
*Color.*—Center of flower—Rose Red, Plate 12, very lightly overcast with Scarlet-Red, Plate 1. Outer petals—Rose Red, Plate 12, very lightly overcast with Tyrian Rose, Plate 12 on the outer edge of the petal. Base of petals (aiglet)—Barium Yellow, Plate 16. Inside of petals—Rose Red, Plate 12. Reserse of petals—Marguerite Yellow, Plate 30, faintly overcast with La France Pink, Plate 1. General tonality from a distance—Rose Red, Plate 12.
*Discloration.*—General tonality at end of first day—Rose Red, Plate 12. Second day — Rose Red Plate 12. Third day—Rose Red, Plate 12, very lightly overcast with Tyrian Rose, Plate 12.

Petals:
*Texture.*—Thick; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Very long; drop off cleanly.
*Fragrance.*—Slight. Nature—tea (average hybrid tea scent).
*Lasting quality.*—On plant—very long. As cut flower—very long.

*Genital organs*

Stamens, Anthers: Small; many; regularly arranged around styles. Color—Orange Buff, Plate 3.
Stamens, filaments (threads): Medium length. Color—Martius Yellow, Plate 4.
Pollen: Color—Capucine Buff, Plate 3.
Styles: Bunched; even; medium length; thin.
Stigmas: Color—Straw Yellow, Plate 16.
Ovaries: All enclosed in calyx.
Hips: None.
Seeds: None.

*Plant*

Form: Bush.
Growth: Vigorous; upright and bushy; averages about 2 feet in height.
Foliage: Compound of 3–7 leaflets.
*Size.*—Medium.
*Quantity.*—Abundant.
*Color.*—New foliage: upper side—Garnet Brown, Plate 1, with mid-rib and serrations Yellowish-Oil Green, Plate 5; under side—Eugenia Red, Plate 13. Old foilage: upper side—Varley's Green, Plate 18; under side—Light Cress Green, Plate 31.
*Shape.*—Oval.

*Texture.*—Upper side — leathery. Upper side — smooth.

*Ribs and veins.*—Ordinary.

*Edge.*—Serrated (saw toothed).

*Serration.*—Both double and single; large.

*Leaf stem.*—Color — Rainette Green, Plate 31. Under side—smooth.

*Stipules*—Medium length; bearded.

Wood:

*New wood.*—Color—Lettuce Green, Plate 5. Bark —smooth.

*Old wood.*—Color—Forest Green, Plate 17. Bark —smooth.

Thorns:

*Thorns.*—Quantity: on main stalks from base— ordinary; on laterals from stalk—ordinary. Form—narrow base; medium length; some straight and some hooked downward. Color (when young)—Spinel Pink, Plate 26. Position—irregular.

*Prickles.*—Quantity: on main stalks—none; on laterals—none.

*Short needles.*—Quantity: on main stalks — none; on laterals—none.

I claim:

A new and distinct variety of rose plant of the floribunda class, substantially as herein shown and described, characterized particularly as to novelty by the unique combination of a prolific production of cut flowers, an attractive and distinctive general color tonality of the flowers, with the inside of the flower petals being Rose Red and the reverse side being Marguerite Yellow, faintly overcast with La France Pink, and long-lasting flower qualities.

No references cited.

ABRAHAM G. STONE, *Primary Examiner.*